(12) United States Patent
Cahill

(10) Patent No.: US 8,792,611 B2
(45) Date of Patent: *Jul. 29, 2014

(54) SINGLE WELL NUCLEAR DENSITY GAUGE

(75) Inventor: Bonaventure Cahill, Crestview Hills, KY (US)

(73) Assignee: Ohmart Corporation (The), Cincinnati, OH (US)

( * ) Notice: Subject to any disclaimer, the term of this patent is extended or adjusted under 35 U.S.C. 154(b) by 267 days.

This patent is subject to a terminal disclaimer.

(21) Appl. No.: 13/190,461

(22) Filed: Jul. 25, 2011

(65) Prior Publication Data

US 2012/0020457 A1   Jan. 26, 2012

Related U.S. Application Data

(63) Continuation-in-part of application No. 12/242,177, filed on Sep. 30, 2008, now Pat. No. 7,986,766.

(51) Int. Cl.
    *G01B 15/02* (2006.01)
(52) U.S. Cl.
    USPC ............................................. 378/54; 378/52
(58) Field of Classification Search
    USPC .................. 378/51, 52, 54; 250/306, 357.1
    See application file for complete search history.

(56) References Cited

U.S. PATENT DOCUMENTS

| | | |
|---|---|---|
| 3,100,841 A | 8/1963 | Reider |
| 3,473,021 A | 10/1969 | Elliott et al. |
| 3,668,392 A | 6/1972 | Bajek et al. |
| 4,580,052 A | 4/1986 | Hoffman et al. |
| 7,214,309 B2 | 5/2007 | Chen et al. |
| 7,238,273 B2 | 7/2007 | Chen et al. |
| 7,986,766 B2 | 7/2011 | Cahill |
| 2006/0163115 A1 | 7/2006 | Montanari et al. |

FOREIGN PATENT DOCUMENTS

| | | |
|---|---|---|
| EP | 2 169 389 A1 | 3/2010 |
| GB | 2059581 | 4/1981 |
| WO | 03/012378 A | 2/2003 |
| WO | 2007/004897 A | 1/2007 |

OTHER PUBLICATIONS

International Search Report Mailed Feb. 16, 2010 in related European application No. 09000721.2-2204.
International Search Report and Written Opinion mailed Dec. 13, 2012, related to PCT/US2012/055751.

*Primary Examiner* — Jurie Yun
(74) *Attorney, Agent, or Firm* — Woods, Herron & Evans, LLP

(57) ABSTRACT

A nuclear density gauge has an elongated transmission chamber adjacent to an elongated source chamber so that they can both be installed through a single nozzle on a high pressure vessel, making an airtight seal with the nozzle. The shape and position of the source chamber allows the positioning of a radiant energy source inside the vessel, a distance from one end of the transmission chamber. The radiation emitted by the radiant energy source travels through contents of the high pressure vessel and then through the elongated transmission chamber to a detector. The method of use of the gauge or multiple gauges, and the adaptation of vessels for such gauges, are also disclosed.

12 Claims, 10 Drawing Sheets

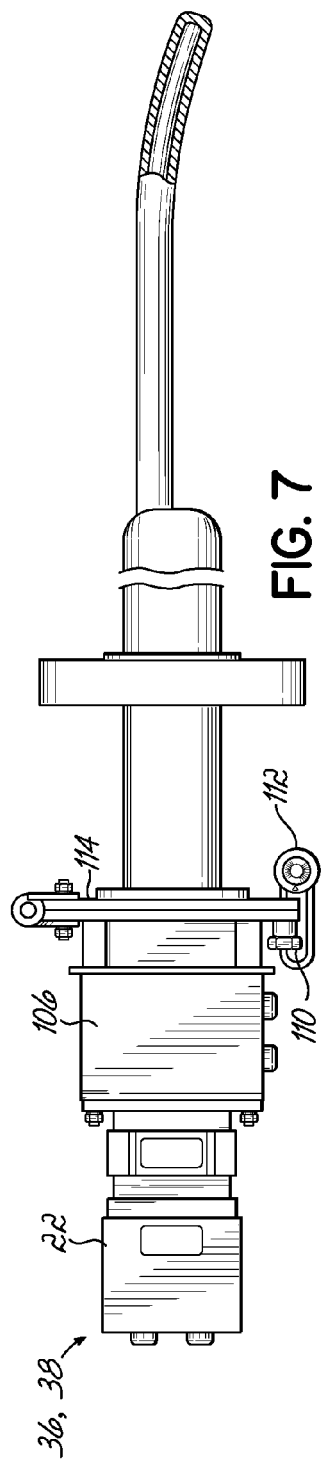
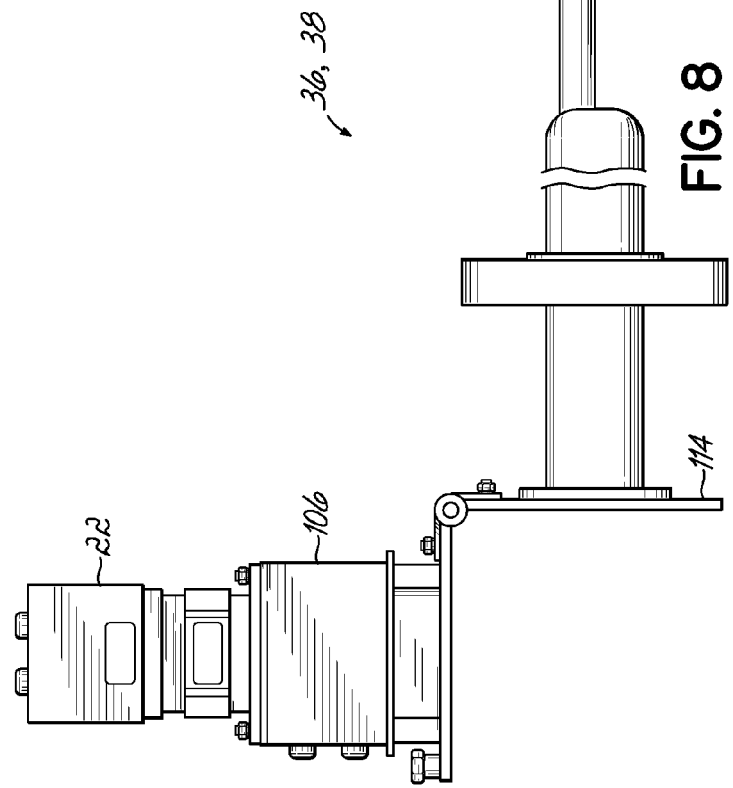

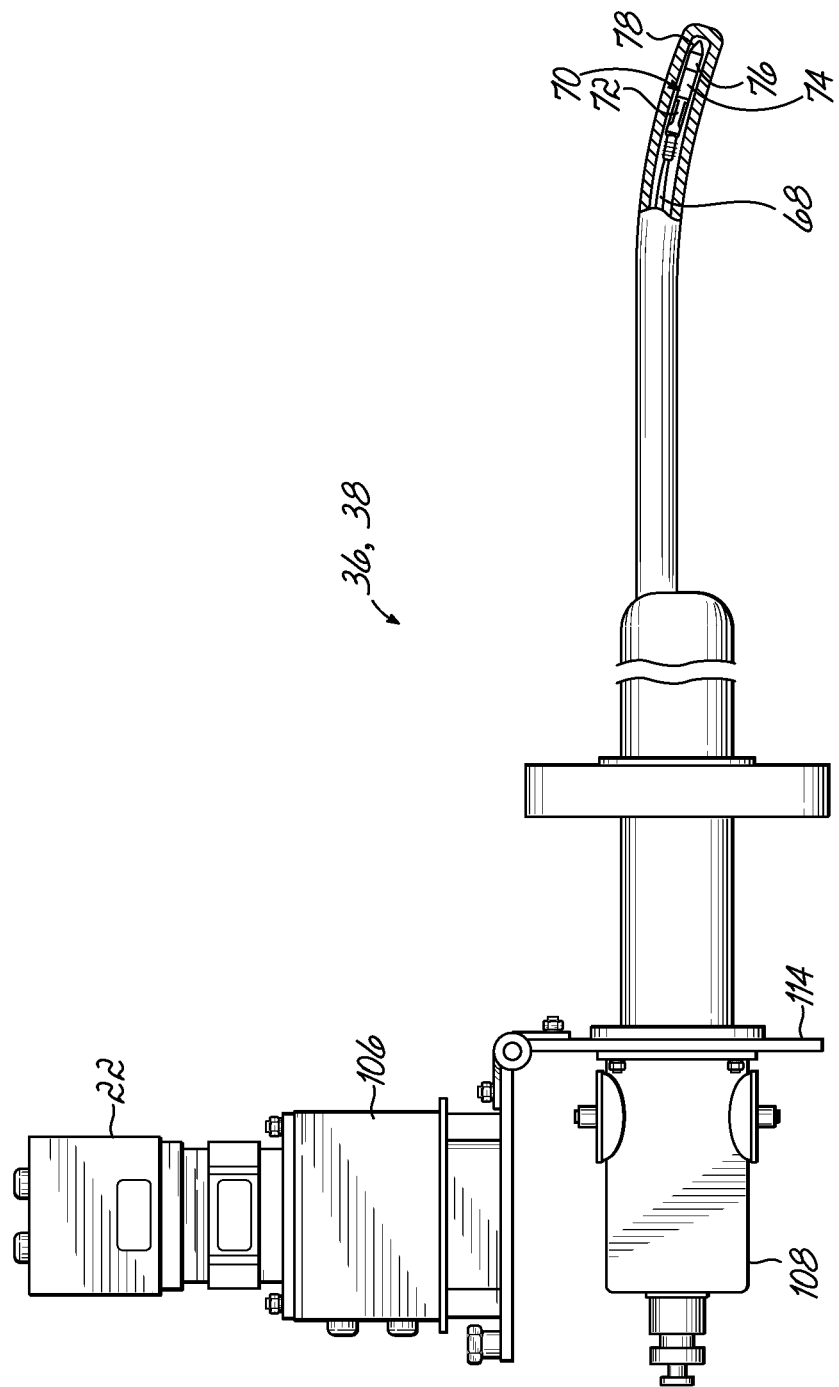

SINGLE WELL NUCLEAR DENSITY GAUGE

CROSS-REFERENCE TO RELATED APPLICATIONS

This Application is a Continuation-in-part of application Ser. No. 12/242,177 filed on Sep. 30, 2008, the entirety of which is hereby incorporated by reference in this application as if fully set forth herein.

FIELD OF THE INVENTION

The current invention relates to measuring properties of the contents in a vessel, more specifically with a nuclear density gauge.

BACKGROUND OF THE INVENTION

Nuclear density gauges are often used to measure liquids (the term liquid, when used in this application for patent, includes slurries) in a vessel at places such as oil refineries. As illustrated in prior art FIG. 1, a nuclear density gauge 10P has two parts that are separated with the liquid to be measured located between them. The first part is a sealed source of radiation 14P, commonly referred to as a "source." The second part is a detector 16P, for example, a scintillation detector. When radiation leaves the source, the amount reaching the detector aligned with the source decreases as the distance between them increases, even if there is only a vacuum between them. When passing through a liquid 18P in a vessel 20P, the mass of the liquid absorbs some of the radiation. In addition to the liquid, if the source, the detector, or both, are located outside the vessel, the radiation must also pass through at least one of the vessel walls 22P. Since the absorption of the radiation by the walls 22P is constant, and the distance between a source 14P and a detector 12P is constant, the amount of radiation reaching the detector is indicative of the density of the liquid 18P it passes through. As the density of the liquid changes, the amount of radiation reaching the detector changes. The greater the density of the liquid, the less radiation reaches the detector. The detector typically provides density measurement in the form of a current output.

It should also be noted, that to keep a detector cool, and make it easier to maintain, detectors 12P are almost always located outside the vessel 20P. The source 14P, however, is durably packaged, and may be placed inside the vessel to be operated in extremes of pressure and temperature safely, using insertion tubes.

In installations where the vessel walls 22P are thin, and the distances across the vessel 20P are small, for example less than two to three feet, a source 14P can be on one side of the vessel, and the detector on the other side as schematically shown in prior art FIG. 1. Such an arrangement is also often used to measure density inside a pipe. Then radiation passes through a first vessel wall, the entire length of liquid, and a second vessel wall before reaching the detector. This works best when the vessel walls are thin and the path through the liquid is short. For liquid density measurements, for example, this arrangement is typically used when the path through the liquid is not greater than two or three feet. For thick walls or long paths, more radiation is absorbed, decreasing measurement sensitivity. Larger sources may be used, but compensating with ever larger sources of radiation becomes impractical.

For larger vessel sizes or greater wall thicknesses, there are ways to decrease the material that must be penetrated. For larger vessels or thicker walls, what is known as an "internal solution" can be used as shown in prior art FIG. 2. An internal solution entails placing the source 14P inside the vessel, and the detector 16P, outside the vessel. This decreases the distance of liquid 18P the radiation passes through, and decreases the number of vessel walls 22P from two to one.

There are also limits on the size of vessel for which the configuration of FIG. 2 is a desired solution. Distance, steel thickness, and liquid density all play a role. A general rule is that 4 inches of water, and ½ inch of steel, have about the same affect on the radiation. However, liquids being measured are not usually only water. As a general rule, if a distance is greater than 2 feet, or steel thickness greater than 2 inches, configurations other than FIG. 1 or FIG. 2 are necessary.

Another internal solution is schematically illustrated in prior art FIG. 3. In this Figure, the vessel wall 22P is thick. At the top of the figure, the wall is locally thinned at 24P. One way of doing this is to drill a hole 26P starting at the exterior, but stopping before reaching the interior. This hole 26P is often called a "detector well" in the industry. The area around the hole 26P is reinforced (not shown) as necessary, for example by welding on additional metal plating. A source 14P is placed in line with the detector. This is done by drilling a hole 28P through the vessel wall and welding in place a nozzle that can accept a sealed tube 30P that can contain the source. The area around the hole 28P is reinforced (not shown) as necessary, for example by welding on additional metal plating. This sealed tube 30P is known as a "source well" and is often referred to as a "dry well." Radiation leaving this source will pass through liquid near the vessel wall and a thin wall 24P to reach the detector.

Another type of detector well 32P is shown in FIG. 3 at the left side of the figure. This detector well fully penetrates the vessel wall through a nozzle with a welded in place sealed tube positioned interior to a detector. Another source well 29P is used to place a source in line with the detector well 32P. Radiation leaving this source will pass through a liquid path close to the center of the vessel, through a relatively thin well wall 33P, through a distance of air 34P, and reach the detector.

The prior art of FIGS. 1, 2, and 3 all have disadvantages, some of which are explained in the following:

As already stated, the configuration of FIG. 1 is limited to smaller vessels and thinner vessel walls.

In FIG. 2, alignment of the sources with the detectors can be difficult to achieve and maintain. It also does not accommodate thick walls. In addition, as vessel pressure and temperature change the vessel expands and the relative position of the sources and detectors changes. Large vessels intended for high pressure and high temperature operation may change length as much as 10 inches when going from ambient to operating conditions. Further, the source well inside the tank is subject to buffeting that may move its location relative to the detector. The detector, mounted outside the tank, may be inadvertently moved relative to the source. In short, the detector and the source are not coupled to one another, and therefore they are subject to different conditions that can move them out of alignment, creating significant measurement errors.

In FIG. 3, the internal solutions, each of which require two holes in the vessel, are undesirable for at least three reasons. First, especially when dealing with high temperatures and pressures, it is preferred that vessel walls not be modified and be left in their full un-cut state, to maintain maximum integrity, without the addition of reinforcements. Second, drilling two precisely aligned holes, for example 26P and 28P, through a thick wall is very difficult. Even if aligned correctly at the start of the drilling, the drill can deflect off course while passing through thick metal. And third, even if the source and detector have a known geometric relationship to one another in a cool vessel, this can change as the temperature and pressure in the vessel changes. This may be further exasperated by the reinforcements placed around the holes that may cause non-uniform metal expansion, and thwart attempts to predict movement.

The need for higher temperature and pressure vessels, and their thick walls, is increasing for a variety of reasons, including processes developed by the refining industry for upgrading heavy-oils. An example of this process is EST (Eni Slurry Technology) being developed by Eni corporation of Italy, as at least partly described in US Published Patent application 2006/0163115. Another example is VRSH (Vacuum Resid Slurry Hydrocracking) developed by Chevron Corporation, as partly described in U.S. Pat. Nos. 7,238,273 and 7,214,309.

Thus, there exists the need for a nuclear density gauge configuration for more accurately and easily measuring the density of a liquid in a thick walled vessel at high temperature and pressures. Such a gauge also has advantages in less severe applications.

SUMMARY OF THE INVENTION

In a first embodiment, a contents measuring gauge has an elongated transmission chamber adjacent to an elongated source chamber so that they can both be installed through a single nozzle on a high pressure vessel, making an airtight seal with the nozzle. The shape and position of the source chamber allows the positioning of a radiant energy source inside the vessel, a distance from one end of the transmission chamber. The radiation emitted by the radiant energy source travels through contents of the high pressure vessel and then through the elongated transmission chamber to a detector.

A second embodiment is a system of gauges of the first embodiment installed in an array of locations varying in longitudinal location, angular location, and radial depth, to determine homogeneity of the contents of the vessel.

A third embodiment is a vessel adapted for single-hole measurement of content density. The vessel has a wall, at least one nozzle in the wall having an elongated transmission chamber and an adjacent elongated source chamber. The elongated source chamber is configured to position a radiant energy source a distance from a one end of the elongated transmission chamber inside the high pressure vessel. The radiation emitted by the radiant energy source travels through contents of the high pressure vessel and then through the elongated transmission chamber to a detector.

A fourth embodiment is a method of measuring a property of contents in a vessel at a particular location in the vessel. In the method, a gauge is installed through an opening of the vessel so that an airtight seal is made. A radiation source is within a portion of the gauge inside the vessel so that the radiation source is in alignment with a transmission chamber of the gauge. The transmission chamber has one end adjacent the contents at the particular location and a second end outside the vessel. The radiation source emits radiation through the contents at the particular location and into the transmission chamber. The emitted radiation that reaches the second end of the transmission chamber is measured, and a signal is created indicative of the property of the contents.

A fifth embodiment is a method for measuring inside of thick tanks having walls that would substantially completely absorb a radiant energy signal of a particular strength radiant energy source. The method includes installing a nuclear density gauge through a single hole in the wall.

In each of the noted embodiments, a reflector may be aligned relative to the source and transmission chamber to redirect radiant energy from the source into the transmission chamber after reflection from the reflector.

BRIEF DESCRIPTION OF THE FIGURES

FIGS. 7, 8, and 9 are an overview of loading a source into the embodiment of FIG. 5.

DETAILED DESCRIPTION OF THE INVENTION

Figure 4:
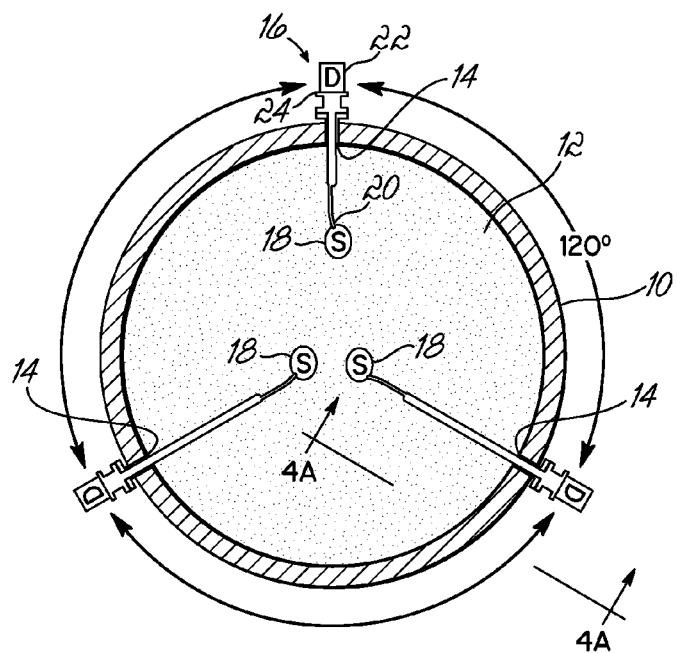
FIGS. 4 and 4A are a schematic illustration of an embodiment of the current invention for comparison to FIGS. 1, 2, and 3.
Figure 4A:
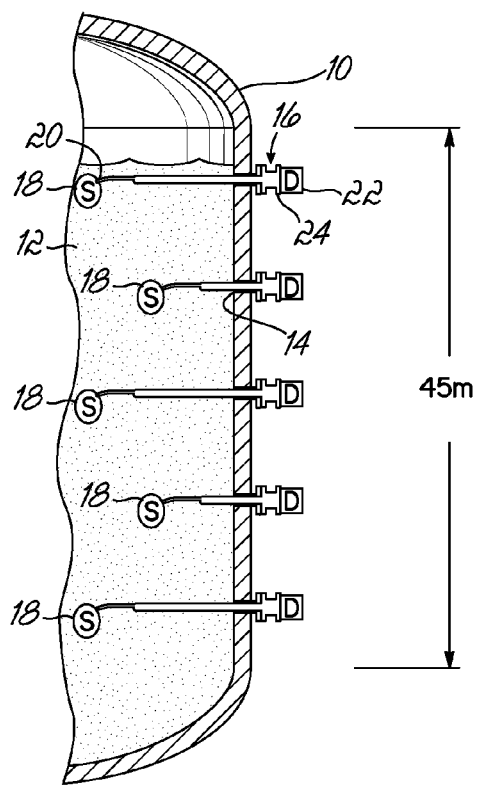

With reference to FIGS. 4 and 4A, a vessel 10 containing a liquid 12 has a plurality of content gauges each installed through a single hole 14. In this embodiment, the content gauges are nuclear density gauges 16, but the single-hole concepts of the current invention may also be used for other gauges. Each nuclear density gauge 16 has a source 18 located at a smaller end 20 inside the vessel, and a detector 22 at a larger end 24 outside the vessel. Alternatively, the detector may be installed at a position inside the boundaries of the vessel 10 if the temperature is suitable, but positioning it outside makes it more accessible for maintenance and cooling. Gauges 16 are installed at various heights and angular locations corresponding to desired density readings of the liquid 12 at particular locations in the vessel 10. There are two different length gauges illustrated. This will be further explained with reference to other figures.

Figure 2:
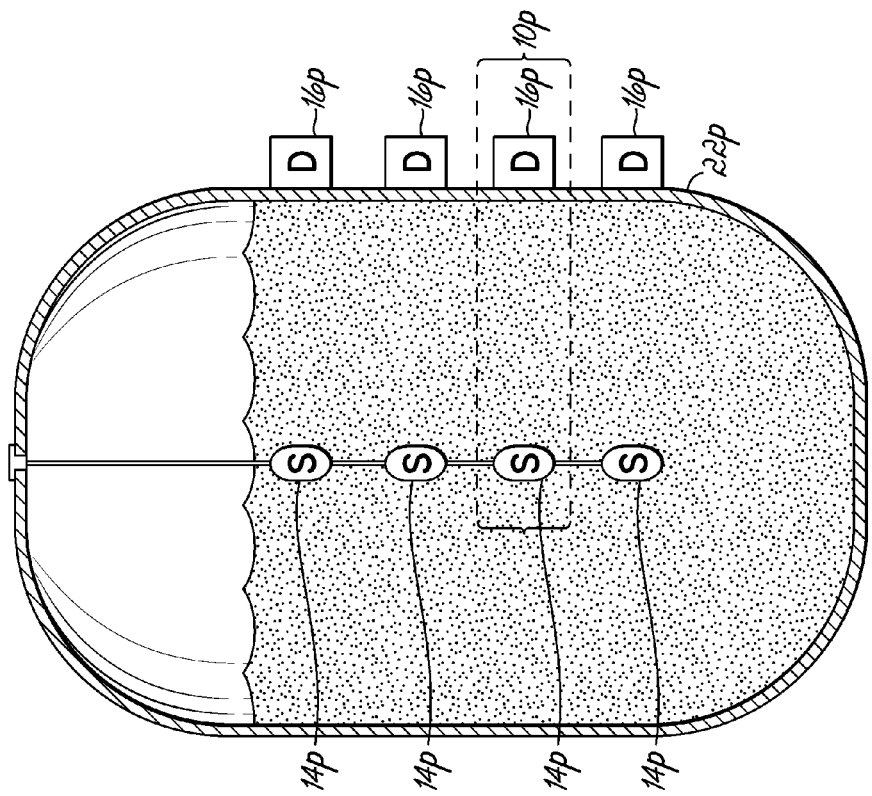
FIG. 2 is a schematic illustration of the prior art for larger thin walled vessels.
Figure 1:
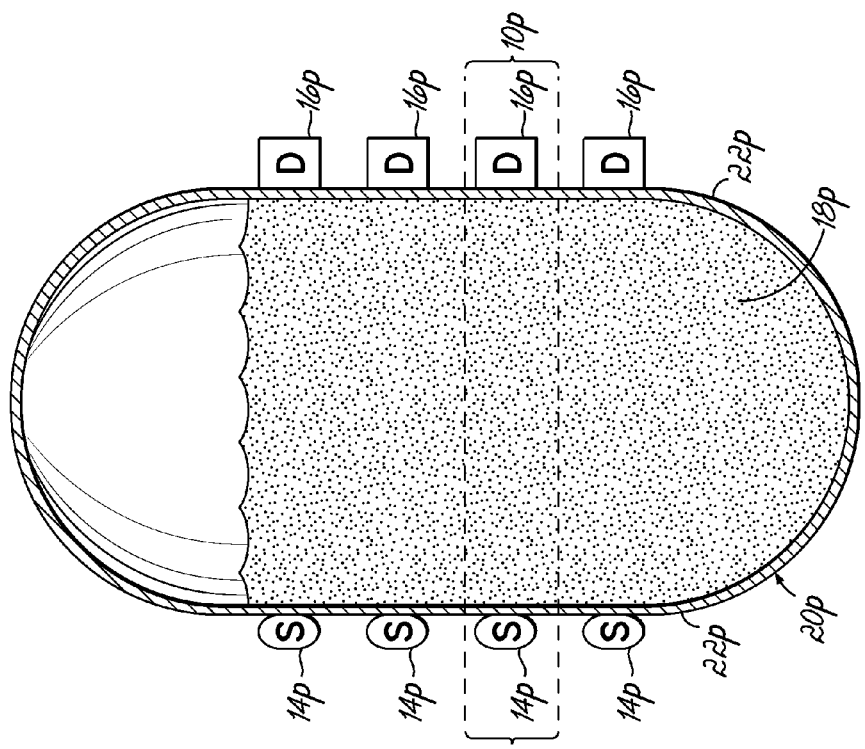
FIG. 1 is a schematic illustration of the prior art for smaller thin walled vessels.
Figure 5:
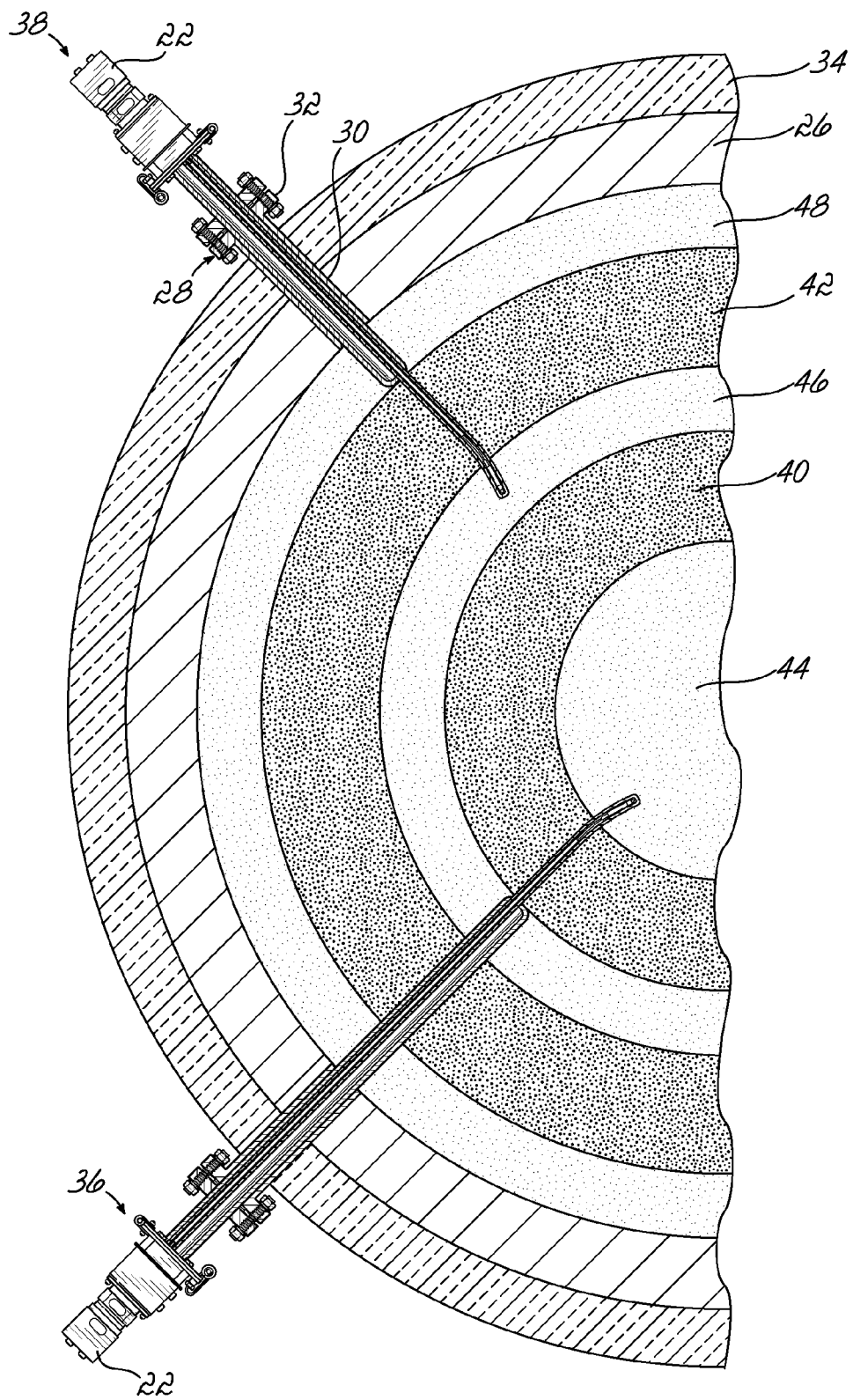
FIG. 5 schematically illustrates an embodiment of the current invention installed in a filled vessel.

In FIG. 5, a vessel wall 26 has a nozzle 28 comprising a cylindrical nozzle body 30 and a nozzle flange 32. The nozzle body 30 is welded to the vessel wall 26, usually by the vessel manufacturer. Outside the vessel wall 26 is a layer of insulation 34. Inside the vessel wall is the liquid 12. In the example of the EST process, for which this gauge 16 is well suited, the contents are a liquid or slurry that may be at high temperature 420° C. (788° F.) and pressure 165 bar (2392 lbs/in2). One vessel for this process is approximately 150 ft. tall, 16 ft. in diameter and has 12" thick steel walls. These parameters preclude the use of conventional instruments including conventional nuclear density gauges as described in prior art FIGS. 1 and 2.

Figure 3:
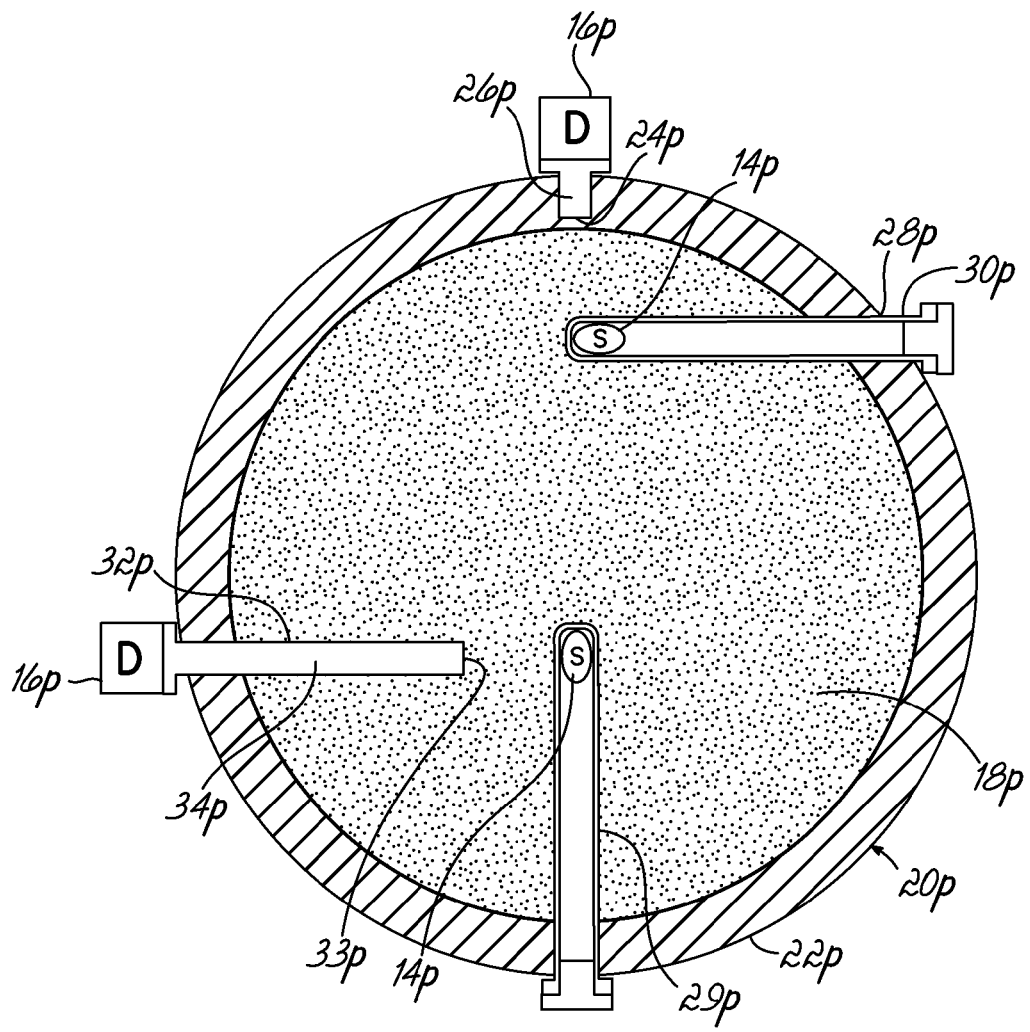
FIG. 3 is a schematic illustration of the prior art for thick walled vessels. It is a cross-section through a cylindrical vessel, although it could also be representative of a spherical vessel.

A gauge 36 is longer and extends nearer the center of the vessel than does a gauge 38. Gauge 36 measures an inner measurement zone 40, and gauge 38 measures an outer measurement zone 42. Zone 44, Zone 46, and Zone 48 do not get directly measured, although with a greater number of gauges, or with gauges of different lengths, they could be measured. That is an advantageously flexible aspect of this invention. By installing longer or shorter gauges, different zones can be measured. Differently drilled pairs of holes, as needed in prior art FIG. 3, are not required to change the zone of liquid 12 that is being measured, or to redefine the size or quantities of measurement zones. The lengths of the gauges define concentric rings, for example 40 and 42, labeled in FIG. 5. This will be understood in more detail from the description that follows of gauge 38 with reference to FIG. 6. In addition, angular locations as depicted in FIG. 4, and height location as depicted in FIG. 4A, further pinpoint the area of liquid measured by a particular gauge. The locations of FIGS. 4 and 4A are representative only, of the ability to measure any location in a vessel that a nozzle is aligned with. By this method, the discreet data can be used to develop a map of the measurements, averages, etc.

Figure 6:
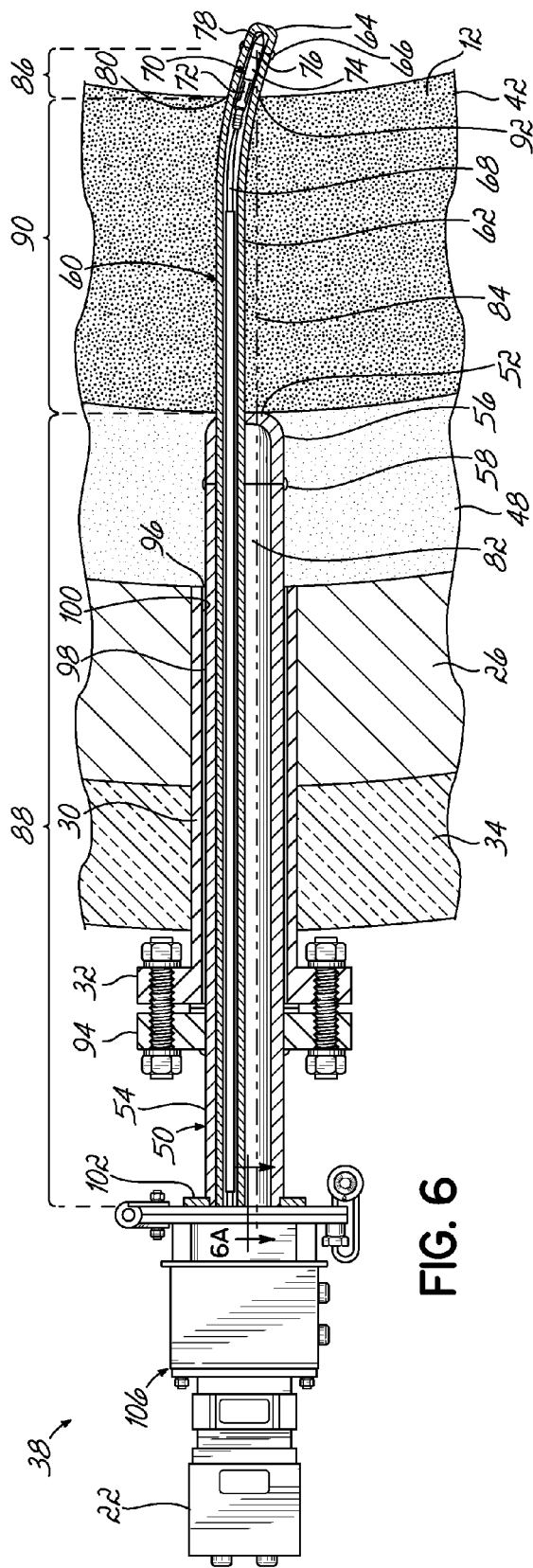
FIG. 6 is an enlarged view of an embodiment in FIG. 5, in partial cross-section, with a radiation path illustrated.

As seen in FIG. 6, gauge 38 has a transmission chamber 50 comprising a transmission wall 52, a transmission outer tube 54, and an end cap 56 secured to the transmission tube 54 by a weld 58. Adjacent the transmission chamber is a source chamber 60 comprising a source tube 62 and an end cap 64 secured to the source tube by a weld 66. Although welded end caps are used for both the transmission tube 54 and the source tube 62, other variations that make a strong sealed tube may be used. Inside the source chamber 60 is a source cable 68, a source carrier 70 comprised of a source shielding rod 72 made of tungsten, a source spacer 74, a source 76 that produces gamma rays in all directions, and a guide nose 78. As seen in FIG. 6, the source tube is not along the center axis of the transmission tube, but is instead to one side (the top, as drawn.) Further, the source tube 62 is straight both inside the transmission chamber 50 and immediately outside the transmission chamber 50 for a considerable distance, but has a radius 80 to align the source 76 over an empty part 82 of the transmission chamber 50. This geometry creates a radiation path 84 comprising three components. Two of these components: a tip path 86, and a chamber path 88, are unaffected by changes in the liquid 12. The third, a process path 90, is affected by changes in the liquid 12, specifically in the outer measurement zone 42. This will be further explained.

The tip path 86 extends from the source 76 in a straight line toward the detector 22, ending outside the wall of the source tube 62 at a point 92. Note that the tip path 86 would be longer if the radius 80 were greater (a larger value), and this difference would mean that the radiation would pass through a longer distance of metal in the wall of the source tube 62. When designing and manufacturing a gauge, this longer distance of metal could lead to a calculated need for a greater source 76 size (strength). If the radius 80 changes during tank heating and cooling, the radius 80 change can lead to erroneous measurements. Therefore, the source tube 62 has a stable and constant radius 80 so that the absorption of gamma rays in the tip path 86 remains constant.

The process path 90 extends from point 92 to the transmission wall 52, and defines the outer measurement zone 42. The absorption of gamma rays along the process path 90 varies with the density of the liquid 12. The measured absorption averages any localized density difference along the process path 90. For this reason, a gauge having a longer process path 90 may measure a different average than one having a shorter process path. The length and location of the process path, and therefore the measurement zone 42, is chosen to match customer needs. The length of the process path may be changed by changing the length of the straight portion of source tube 62. Because the process path 90 is a function of the gauge construction and is not dependent upon vessel dimensions and successful mounting on the vessel, the gauges of the current invention may be calibrated without being installed in the vessel.

The chamber path 88 includes the metal of the transmission wall 52 and the air in the empty part 82 of the transmission chamber 50, as well as any intersected metal used to mount and protect the detector 22. To minimize the size of the needed source 76, the metal intersected by the chamber path 88 is kept to a minimum, however the transmission wall 52 must be thick enough to withstand the pressure within the vessel 10. Further, since radiation intensity decreases with distance, the longer the chamber path, the greater the calculated source required, even if the radiation is passing through a vacuum.

As seen in FIG. 6, a primary flange 94 is welded to the transmission tube 54, and fastened to the nozzle flange 32 in an appropriately strong and sealing arrangement. This connection seals the vessel 10. The high pressure liquid 12 is free to move into a gap 96 between an outside 98 of the transmission tube 54 and an inside 100 of the nozzle tube 30, but is stopped by the primary flange 94.

Figure 6A:
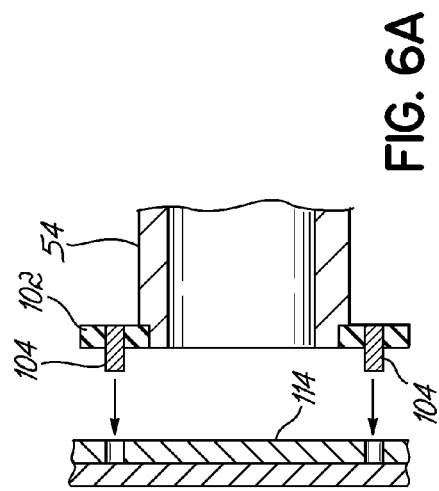
FIG. 6A is an exploded cross-section view as indicated in FIG. 6.

Referring to FIGS. 6 and 6A, the transmission tube 54 has a secondary flange 102 that is thinner than the primary flange 94 and does not need to withstand pressure. Secondary flange 102 aligns the detector, as well as devices used to install and remove the source 76 from the source chamber 60. As such, the secondary flange 102 has two alignment pins 104 and bolt holes (not shown) for mounting the detector 22. A water-jacket housing 106 cools the detector 22.

FIGS. 7, 8, and 9 illustrate the general process of loading the source 76 into the source chamber 60. It is not the intent here to fully describe the safe storage and insertion of the radioactive source 76. Systems such as a source housing 108 already exist to shield and transport the source carrier 70 until it is placed in its working position away from personnel. The presentation of these figures merely serve to show that the radius 80 does not prevent source carrier 70 insertion. In FIG. 7, a gauge 36 or 38 is represented schematically, as it would be when it is installed in the nozzle 28, but not yet loaded with the source carrier 70. A locking screw 110 is prevented from opening by a padlock 112. In FIG. 8, the padlock 112 is removed and the locking screw 110 released so that the detector 22 and its housing 106 may be rotated away from a stationary plate 114. In FIG. 9, the source housing 108 has been installed for the purpose of inserting the source carrier 70 to the bottom of the source chamber 60 by pushing it with the source cable 68. After this operation, the source housing 108 is removed but the source cable 68 and source carrier 70 remain, ensuring that the source 76 is kept in its fully inserted position. The gauge 36, 38 is then operational, as shown in FIG. 6.

Figure 11:
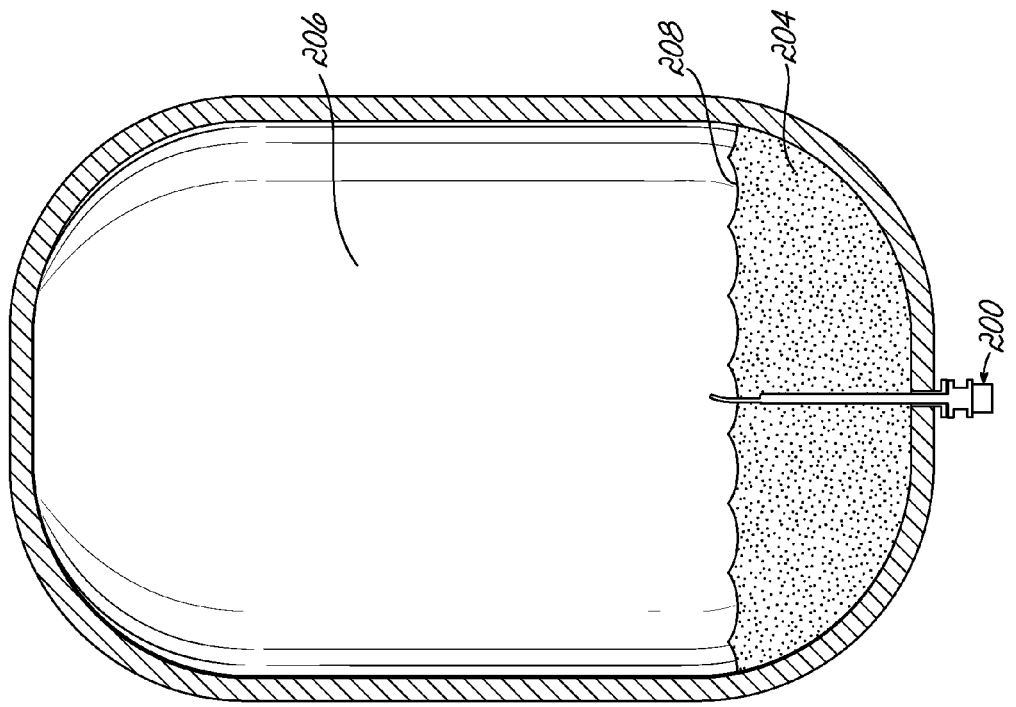
FIGS. 10 and 11 are schematic illustrations of an embodiment of the current invention used to determine level.
Figure 10:
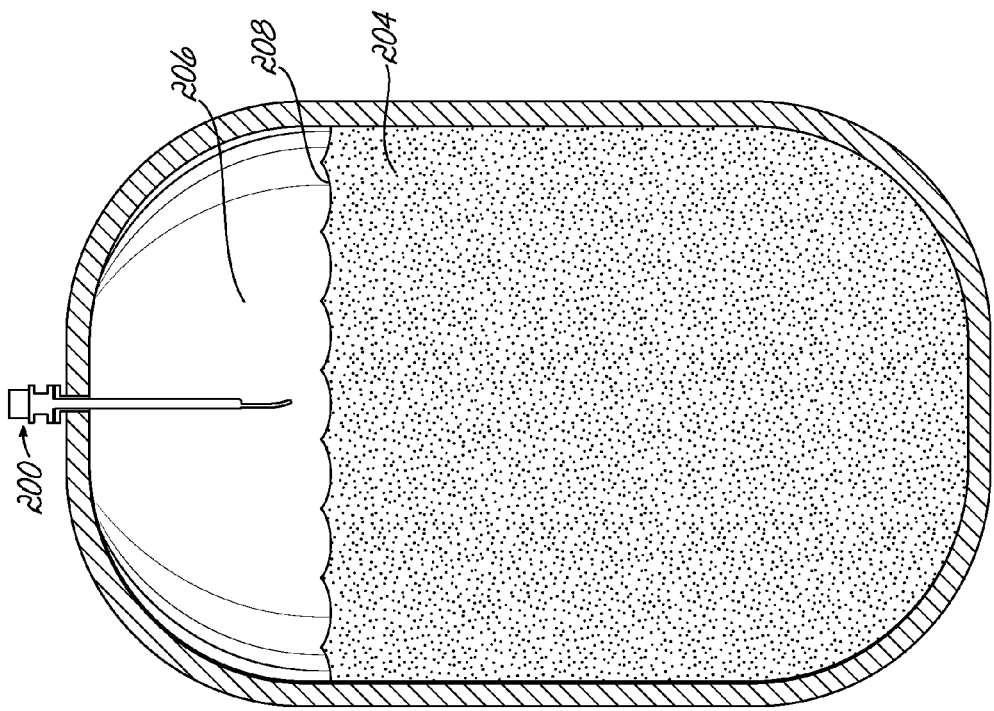

FIGS. 10 and 11 illustrate a method of using a gauge 200 to measure level. In previous figures, the process path 90 was fully submerged in the liquid 12, therefore any change in measurement indicated a change in the average density of the liquid 12 in the process path. By positioning the gauge 200 so that its process path includes a boundary 208 between liquid 204 and vapor 206 (or air), the gauge can be used to measure a level as in FIG. 11, or an absence of liquid as in FIG. 10. Either of these measurements can be taken by a gauge installed from either a bottom or a top of the vessel. Similarly, a side nozzle 28 could be used, if that side nozzle were in the vessel angled upwardly or downwardly.

Figure 12:
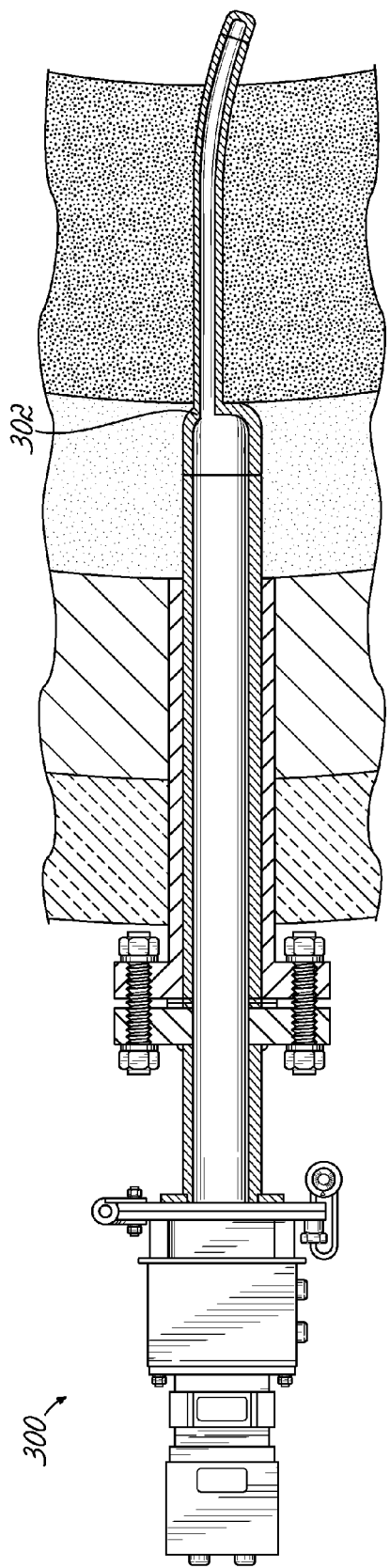
FIG. 12 is another embodiment of the current invention.

FIG. 12 illustrates another embodiment of a gauge 300, to a level of detail showing differences to gauges 36, 38. In this embodiment, the portion of the source chamber 60 inside the transmission chamber 50 is eliminated, as seen at 302. This embodiment may be used with alternative methods of installing sources. For example, the entire gauge 302 may be removed from the vessel 10 and manipulated vertically to get the source 76 in and out of the source chamber 60 by using gravity.

Figure 13:
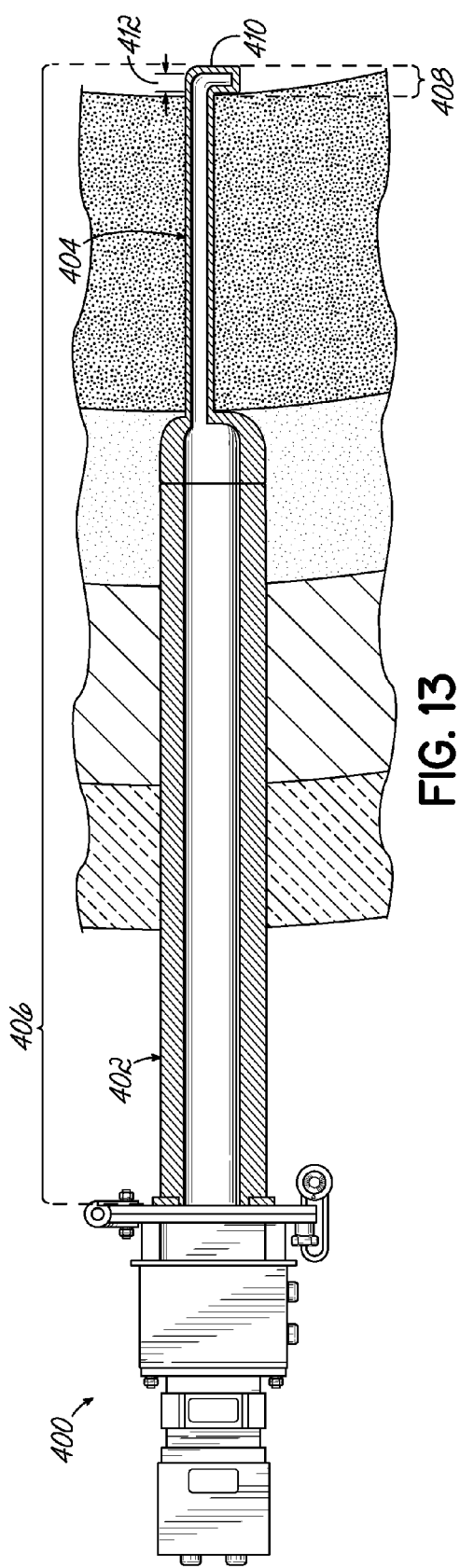
FIG. 13 is another embodiment of the current invention.

FIG. 13 illustrates an embodiment 400 of the invention in which a transmission chamber 402 and a source chamber 404 are made part of a nozzle 406 of the vessel 10. This eliminates the need for the nozzle flange 32 and primary flange 94 to contain the pressure of the vessel 10, and reduces material costs. An area 408 at an end cap 410 is shown right angled, rather than with a radius 80. This is for the purpose of illustrating that the concept of this invention, having a single-hole gauge, is not limited to a radiused source tube. A radiused source tube is simply one way to achieve a source installation and removal consistent with currently available methods. This right angled configuration is not limited to any particular embodiment. The right angle provides a smaller tip path length 412 having less metal than the tip path 86 of radiused source chamber.

Figure 14:
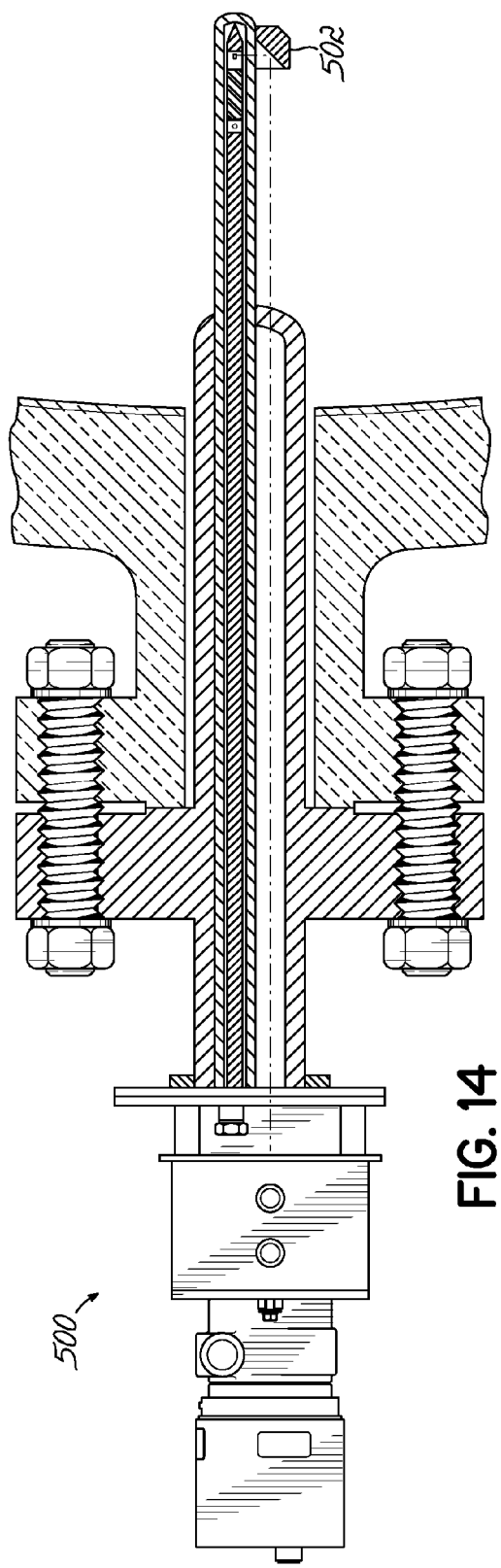
FIG. 14 is another embodiment of the current invention.

FIG. 14 illustrates an embodiment 500 of the invention in which the radiant energy from the source which is at the interior end of the source chamber, is reflected back through the transmission chamber by operation of a reflector 502. This embodiment has the potential advantage that the source chamber does not need to be curved at its interior end to form a straight line path from the source to the detector through the transmission chamber, as radiant energy is reflected into that chamber by the right angle reflector 502 attached to the end of the source chamber.

Figure 15:
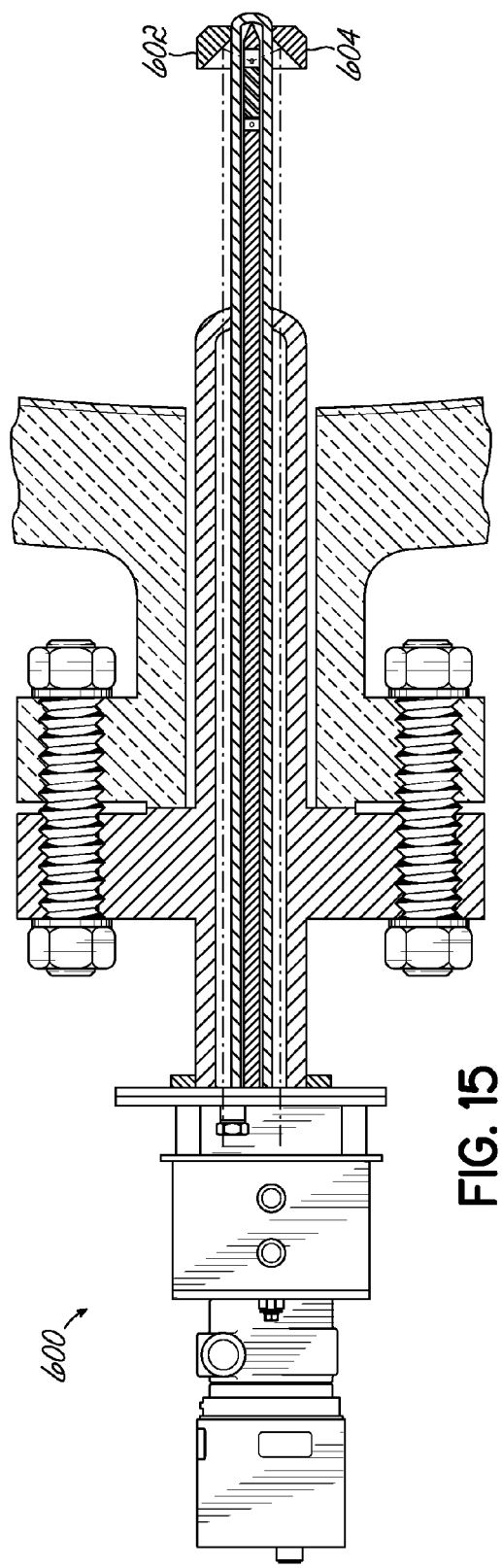
FIG. 15 is another embodiment of the current invention.

FIG. 15 illustrates a still further embodiment 600 of the invention in which radiant energy from the source is reflected back to the detector. In this embodiment, there are dual transmission chambers on opposite sides of the source chamber, and dual reflectors 602 and 604 which reflect radiant energy back through the respective transmission chambers to the detector. This embodiment has the possible advantages of the embodiment of FIG. 14 and the potential further advantage of providing redundant detection within the vessel by virtue of the dual radiant energy paths and dual transmission chambers.

A specific design of a density gauge serves as an example of the invention described. In the specific design, a source tube 62 made of 1 and ¼ inch 0.382 wall 347 stainless steel pipe has a radiation path 84 that passes through 1.532 inches of wall as part of the tip path 86. The process path 90 is 18.752 inches long, ending at a transmission wall 52 0.674 inches thick that is part of a transmission chamber 50 made of 4 inch diameter double extra heavy 0.674 wall 347 stainless steel pipe. For the gauge 38 measuring the outer measurement zone 42 the source size will be 50 mCi (milliCuries) Cs-137. The source will be 100 mCi (milliCuries) Cs-137 for gauge 36 measuring the inner measurement zone 40. Even though these two process paths 90 and tip paths 86 are the same, the differing lengths of the chamber paths 88 lead to using sources 76 of different strength. Although Cesium is used in the specific example just described, the invention does not preclude using other sources, for example, Cobalt. For nuclear density measurements Cesium and Cobalt gamma radiation are often used, but the invention may have broader applications using other forms of radiant energy from other sources, measuring properties other than density or level.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A contents measuring gauge comprising:
   an elongated transmission chamber;
   an adjacent elongated source chamber;
   the chambers sized and positioned together so that they can be installed through a single nozzle on a high pressure vessel, making an airtight seal with the nozzle; and
   a reflector positioned to reflect radiation emitted at a first end of the elongated source chamber inside the high pressure vessel in a straight line through contents of the high pressure vessel and then through the elongated transmission chamber to a detector.

2. A contents measuring gauge as in claim 1 wherein the detector is outside the high pressure vessel.

3. A contents measuring gauge as in claim 2 wherein the reflector reflects gamma rays.

4. A contents measuring gauge as in claim 3 wherein the detector is a scintillation detector.

5. A contents measuring gauge as in claim 4 that measures the density of the contents of the high pressure vessel.

6. A contents measuring gauge as in claim 1 that measures the level of the contents of the high pressure vessel.

7. A contents measuring gauge as in claim 1 wherein the elongated transmission chamber is a first tube and the elongated source chamber is a second tube positioned inside the first tube and extending through a first end of the elongated transmission chamber.

8. A contents measuring gauge as in claim 1 used in the EST process.

9. A contents measuring gauge as in claim 1 used in the VRSH process.

10. A system of gauges as in claim 1 further comprising an array of locations varying in longitudinal location, angular location, and radial depth to determine homogeneity of the contents of the vessel.

11. A vessel adapted for single-hole measurement of content density comprising:
    a vessel wall;
    at least one nozzle in the wall having an elongated transmission chamber, an adjacent elongated source chamber and a reflector, wherein the reflector is configured to reflect radiant energy from a radiant energy source inside the vessel so that the radiation emitted by the radiant energy source travels line-of-sight through contents of the vessel and then through the elongated transmission chamber to a detector.

12. A method of measuring a property of contents in a vessel at a particular location in the vessel comprising:
    installing a gauge through an opening of said vessel so that an airtight seal is made;
    positioning a radiation source within a portion of the gauge inside the vessel;
    positioning a radiant energy reflector inside the vessel in alignment with the radiation source; positioning a transmission chamber of the gauge that is disposed with a first end adjacent the contents at the particular location and a second end outside the vessel;
    emitting radiation from the radiation source via the reflector through the contents at the particular location and into the transmission chamber;

measuring the emitted radiation that reaches the second end of the transmission chamber;

providing a signal indicative of the property of the contents.

* * * * *